United States Patent [19]

McNally et al.

[11] Patent Number: 4,890,457
[45] Date of Patent: Jan. 2, 1990

[54] METHOD FOR CRYOPRESERVING HEART VALVES

[75] Inventors: Robert T. McNally; Albert Heacox; Kelvin G. M. Brockbank, all of Marietta, Ga.; Harvey L. Bank, Charleston, S.C.

[73] Assignee: CryoLife, Inc., Atlanta, Ga.

[21] Appl. No.: 95

[22] Filed: Jan. 2, 1987

[51] Int. Cl.⁴ .............................................. F25D 13/04
[52] U.S. Cl. ........................................... 62/65; 435/1; 435/2; 128/DIG. 27
[58] Field of Search ........................ 435/1, 183, 2, 260; 62/78, 62-65; 128/362, 898, DIG. 27

[56] References Cited

U.S. PATENT DOCUMENTS

| | | |
|---|---|---|
| 3,303,662 | 2/1967 | Moline . |
| 4,008,754 | 2/1977 | Kraushaar et al. . |
| 4,134,359 | 1/1979 | Redpath . |
| 4,388,814 | 6/1983 | Schilling ................................. 62/78 |
| 4,423,600 | 1/1984 | McKenna ............................... 62/78 |
| 4,429,542 | 2/1984 | Sakao et al. ............................ 62/78 |
| 4,455,842 | 6/1984 | Granlund ............................... 62/78 |
| 4,464,337 | 8/1984 | Zelman . |
| 4,537,034 | 8/1985 | Crouch . |
| 4,559,298 | 12/1985 | Fahy ...................................... 62/78 |
| 4,597,266 | 7/1986 | Entrekin ............................. 62/457 |
| 4,688,387 | 8/1987 | Conaway ................................ 62/78 |

OTHER PUBLICATIONS

An Organic Cryopreservation Apparatus, Michael G. O'Callaghan et al., IEEE Transactions on Biomedical Engineering, vol. BME-24, No. 2 (Mar. 1977).
Preservation of Aortic Heart Valves with Maintenance of Cell Viability, Arthur W. M. Van der Kamp, M.D. et al., Journal of Surgical Research 30, 45–56 (1981).

Primary Examiner—Barry S. Richman
Assistant Examiner—T. J. Wallen
Attorney, Agent, or Firm—Jones, Askew & Lunsford

[57] ABSTRACT

A method of freezing, storing and thawing collagen-rich tissue, such as heart valves. The method includes a freezing profile for freezing the tissue down to the temperature of liquid nitrogen with minimal tissue damage due to ice crystal formation. Heart valves cryopreserved according to the present process exhibit a high cell viability when thawed and are suitable for implanting in human patients.

10 Claims, 1 Drawing Sheet

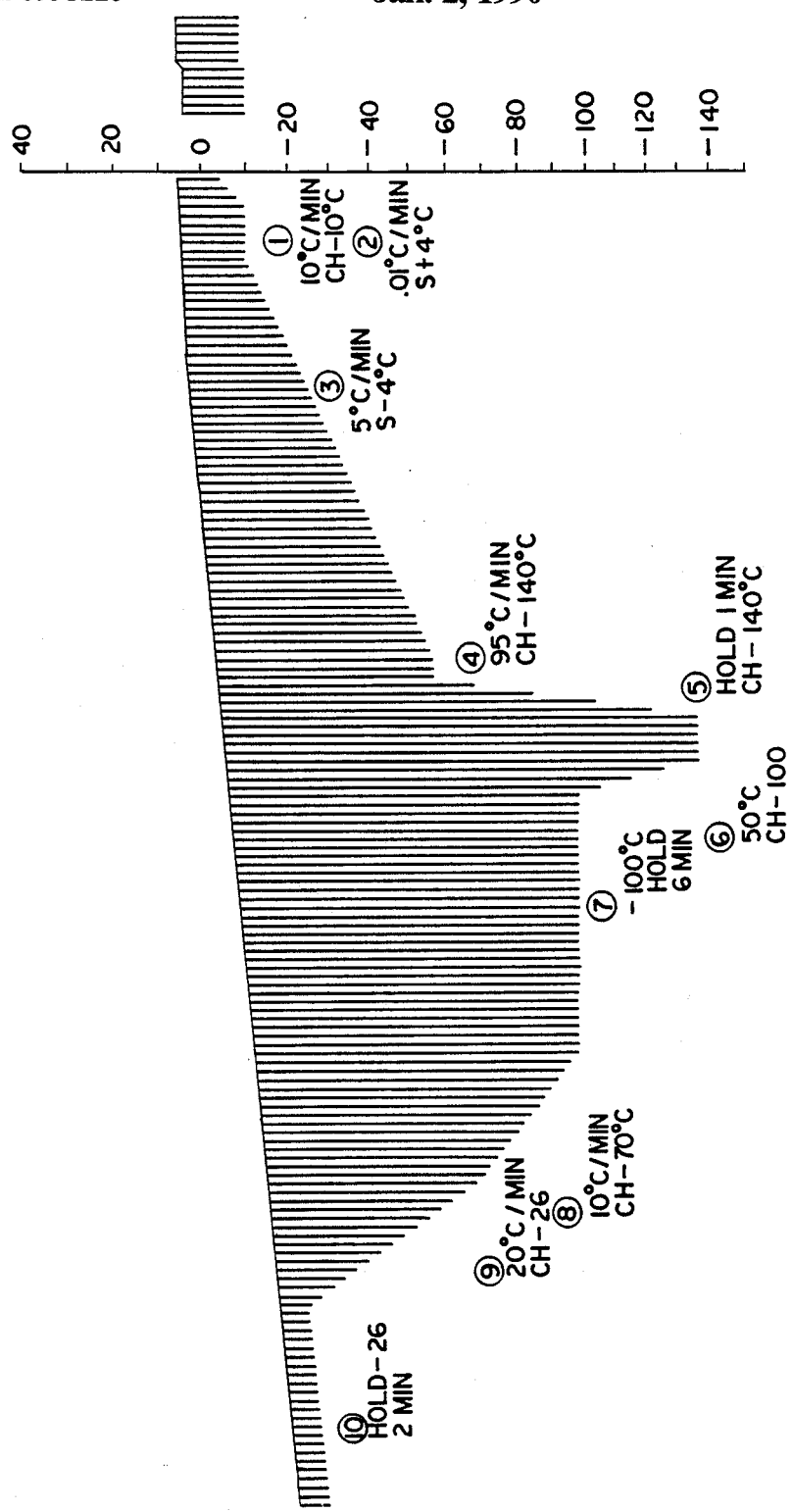

METHOD FOR CRYOPRESERVING HEART VALVES

TECHNICAL FIELD

The present invention relates to a method for cryopreserving heart valves and more particularly to a method for freezing heart valves to ultra-cold temperatures whereby the valves can be stored for long periods of time. Valves cryopreserved according to the present invention are suitable for use as replacement valves in hearts with diseased or malfunctioning valves.

BACKGROUND OF THE INVENTION

Biological aortic valve replacement began in approximately 1962. This early work was initiated because artificial heart valve replacements were plagued with mechanical breakdown and the requirement to anticoagulate the patient.

Biological valves, usually porcine or bovine origin, had the overall advantage of identical design and structure to that of the valve being replaced. Today, approximately 18,000 out of 36,000 total valves replaced in United States each year are tissue valves. Virtually all of the 18,000 biological valves are of bovine or porcine origin, glutaraldehyde-fixed and mounted on a mechanical stent. However, these types of biological valves are non-living. Consequently, time and biological reaction to the non living material work to degrade the tissue until its eventual malfunction.

Because of the inherent problems in using non-living heart valves of animal origin, researchers have begun using human allograft heart valves for replacement of defective heart valves. The human allograft valve is useful either by itself or in association with its conduit, i.e., the aorta with the aortic valve or the pulmonary valve with the pulmonary artery, for use as a crucial constituent in congenital heart repair. Pulmonary outflow tract reconstruction using aortic and pulmonary valve conduits are used routinely for complex tetralogy of fallot, pulmonary atresia, truncus arteriosus and complex transposition of the great arteries. Heretofore, for these congenital defects which occur in eight out of every one thousand births, artificial valves were used in conjunction with artificial vascular conduits. These reconstructive procedures are subject to the same deleterious clinic effects of calcific degeneration and thrombo embolic occurrences as with a non-allograft valve used alone.

Investigators have generally agree that fresh tissue gives improved performance over old or dead tissue, and viable human tissue exceeds the useful performance of the bovine/porcine xenograft valves. However, viable tissue remains alive for only short periods of time. The fibroblast cells, which are the major constituent of the valve leaflet and are the cells which are most important for proper valve functioning and longevity, will remain viable for, at most, two or three days in a life sustaining media. Storage for two or three days is impractical for all but a few of the valve recipients because the valve size of the donor tissue is unlikely to be the correct size for the waiting recipient. Consequently, much of the tissue can not be used for valve replacement because of a severe loss of cell viability with time. Additionally, preservation time becomes increasingly more important in light of the fact that increasing evidence exits for improved tissue performance if the donor and recipient are of the same ABO blood group.

A number of investigators have devised various methods to extend storage life of heart valves. Prior art techniques, such as freeze drying, glutaraldehyde fixation, and mechanical freezing, combined with sterilization techniques of irradiation and antibiotics generally lead to early failure of the tissue.

The storage of cells and tissues became possible after the discovery in 1949, by Polge, Smith, and Parks, that glycerol could be used to protect cells from injury due to freezing. With the advent of low temperature biology, workers in medical and biological fields have been seeking better ways to maintain the viability of frozen donor cells or tissues.

Several methods for freezing cells and cell aggregates have been reported. U.S. Pat. No. 3,303,662 discloses a process for cell preservation which utilizes a cryoprotectant in the freezing process. U.S. Pat. No. 4,423,600 discloses a method for preservation of living organic tissue by freezing which involves lowering atmospheric pressure surrounding the tissue before freezing.

Several attempts have been made to freeze heart valves to ultra-cold temperatures. (e.g., Van der Kemp, et al., *Journal of Surgical Research*, Vol. 30., 47–56, 1981). However, even with the realization that enzymatic degradation of the tissue during long-term storage is minimal at the ultra-cold temperatures of liquid nitrogen, a multitude of problems have been encountered in the implementation of this technology. What is needed, is a method of freezing heart valves to ultra-cold temperatures that will maintain maximum viability of individual cells within the tissue with minimal tissue degradation. The method should allow long term storage of the biological tissue.

SUMMARY OF THE INVENTION

The present invention is a method of freezing, storing and thawing collagen-rich tissue, such as heart valves, with a cell viability of at least 70% after thawing. The collagen-rich tissues that are frozen according to the present invention can be stored for long periods of time at super cold temperatures with minimal loss of cell viability. The present invention provides a unique freezing profile that allows a collagen-rich tissue, such as heart valves, to be frozen down to the temperature of liquid nitrogen, approximately −196° C., with minimal tissue damage due to ice crystal formation. The present invention also includes a thawing schedule whereby the frozen tissue can be rapidly thawed with minimal tissue damage. Heart valves that are cryopreserved according to the present invention are alive when thawed and are ideally suited for replacing diseased or malfunctioning heart valves in heart patients.

Accordingly, it is an object of the present invention to provide a method for cryopreserving a human heart valve so that the valve is viable and functional when thawed.

It is another object of the present invention to provide a method for preserving a viable human heart valve for long periods of time.

It is yet another object of the present invention to provide a unique freezing schedule for freezing a heart valve so that the heart valve cells maintain a high viability after it is thawed.

It is yet another object of the present invention to provide a method for cryopreserving a human heart valve which allows rapid thawing of the heart valve while maintaining maximum cell viability.

It is yet another object of the present invention to provide a viable heart valve that is suitable for transplantation after long term storage at ultra-cold temperatures.

These and other objects, features, and advantages of the present invention will become apparent after review of the following detailed description of the disclosed embodiment and the appended claims.

Brief Description of the Figure

FIG. 1 is a schematic representation of the freezing profile for freezing a heart valve according to a preferred embodiment of the present invention.

DETAILED DESCRIPTION OF THE PREFERRED EMBODIMENT

The present invention is a method of freezing, storing and thawing collagen-rich tissue, such as heart valves, with a cell-viability of at least 70% after thawing. The collagen-rich tissues that are frozen according to the present invention can be stored for long periods of time at super cold temperatures with minimal loss of cell viability. The present invention includes a unique freezing profile that allows a collagen-rich tissue, such as heart valves, to be frozen down to the temperature of liquid nitrogen, approximately −196° C., with minimal tissue damage due to ice crystal formation. The present invention also includes a thawing schedule whereby the frozen tissue can be rapidly thawed with minimal tissue damage. Heart valves that are cryopreserved according to the present invention are biologically viable when thawed and are ideally suited for replacing diseased or malfunctioning heart valves in heart patients.

The tissue to be preserved is only as good as that received into the laboratory. Consideration must be given to donor age, health and history of cardiovascular disease. Another important consideration is the time between death and the harvest of the valves (warm ischemia) and the time from the harvest of the valves to dissection (cold ischemia). Attention must be paid to the method of handling the tissue during procurement and the medium which is used to ship the tissue.

A donor heart that can be used as a source of human heart valves to be frozen according to the present invention should be from donors in the age range of birth to 55 years of age and the donor should not have suffered from significant hypertension, diabetes, communicable disease or cardiac tissue abnormality.

Dissection of the heart must be accomplished within the twenty-four hour time constraints to maximize cell viability. In addition, the dissection must be carried out in such a manner as to disrupt the tissues as little as possible and to remove only the unnecessary adventicia. The method should also incorporate minimal handling and the tissue must be kept moist.

In practicing the present invention, there are two aspects to sterilization of the tissue which require attention. First, the combination of sterilization medium must be toxic to the cells; and second, it must sterilize the tissue. The effects of antibiotics vary with the type of cell or cell suspension that is being preserved and the type of antibiotic being used. The effects of a particular antibiotic on a particular cell must be well documented. The time and temperature at which the antibiotics will be used is also of critical importance. It must be understood that if the tissues remain sterile throughout the harvest and dissection process, no antibiotics are necessary.

The medium in which the tissue is frozen is of great importance for maintaining a balanced cell environment. Time and temperature also contribute to whether a particular medium will be successful. Generally, a protein suspension, such as blood serum or artificial serum, must also be present for maximum cell viability.

A number of freezing media can be successfully used in practicing the present invention. Media such as balanced tissue culture media or simple phosphate buffered saline, can be used for most tissue types. RPMI 1640 (KC Biologicals, Kansas City, Missouri) with 10% fetal calf serum is the preferred combination for heart valves. Other media of a somewhat less acceptable nature are: Eagle's minimum essential medium, TC199, and others.

A cryoprotectant is added to the freezing media to protect the cell during the freezing and thawing phases of the present invention. Care must be taken to prevent osmotic shock and cytotoxicity when using many of these cryoprotectants. Cryoprotectants serve to protect the cells, particularly during the ice crystallization phase, and during the cell shrinkage phase just prior to crystallization. Issues, such as tissue toxicity as related to time, temperature, pressure, and rate of mixing to reach osmotic equilibrium, must be considered in a successful freezing method. Commonly used cryoprotectants include, but are not limited to, glycerol, ethylene glycol, dimethylsulfoxide with acetamide or propylene glycol, or propylene glycol alone, trimethylamine acetate, and a variety of aldoses and ketones, such as xylose, erythrose, arabinose, ribose, glucose, fructose, and galactose or combinations thereof.

It is believed that the function of the cryoprotectants is to partially replace water inside the cell. As water crystals form in the extracellular medium, the hypertonic shrunken state of the cell could, without the cryoprotectant, result in the disruption of cellular components resulting in the death of the cell. Therefore consideration must be given to the rate at which the cryoprotectant is added, the concentration of the cryoprotectant, and the temperature at which the cryoprotectant is added.

The freezing profile is of critical importance to successful cryopreservation of a tissue. A multitude of variables exist to maximize tissue survival. For instance, the volume of fluid, the size of the tissue, and the combination of characteristics incorporating cryoprotectant tissue, and freeze media all contribute to an optimal freezing profile. It is to be understood that the prior art freezing profiles available for cell suspensions are not suitable for freezing tissue, such as heart valves. It has been determined that each tissue has its own unique and unpredictable freezing profile. The freezing profile required to successfully cryopreserve one tissue is unexpectedly different from the freezing profile required to successfully cryopreserve another tissue.

A number of factors need to be considered when freezing a tissue. Among these factors are: the temperature around the equilibrium point, (generally +4° C., to the temperature at the freezing point); release and control of the exothermic heat given off at the freezing point; optimum cooling rate as determined by the permeability of the cell membrane to water; the surface to volume ratio of the cell; the type and concentration of cryoprotective agents in the media; and, finally, removal of the cryopreserved tissue from the controlled rate freezing to an immersion into liquid nitrogen refrigerator.

The thawing and diluting steps with an allograft must be clearly defined, since crystal growth and osmotic shock can still harm the tissue. It has been determined that a thawing rate of 50° C. per minute is appropriate for human heart valves. Once thawed, the cryoprotectant of choice must be removed, usually in a stepwise fashion, to lessen the effects of osmotic shock to the cells and thus allow for an orderly equilibration of the cell with the surrounding medium. Time and temperature are major considerations.

Thus, the method of cryopreserving heart valves according to the present invention comprises dissecting the heart valve from the donor hearts, sterilizing the tissue with a mixture of antibiotics, placing the valves into a medium with the proper cryopreservative agents, freezing the valves according to a precise freezing schedule. The freezing schedule used to cryopreserve the heart valves in the present invention comprises placing the sample into a sample freezing chamber in a cryopreservation apparatus. The initial temperature of the sample chamber is above freezing and is usually approximately +22° C. The temperature of the sample chamber is decreased at a rate of 0.01° C. per minute until the sample chamber reaches a temperature of −2° C. The temperature of the sample chamber is then decreased at a rate of 1° C. per minute until the sample chamber reaches a temperature of −80° C. The heart valve is then transferred to a liquid nitrogen storage device wherein the valve is preserved at a temperature of approximately −196° C. until the valve is to be transplanted into a living heart.

The frozen heart valve is thawed by the following general procedure. A foil pouch containing the frozen heart valve is placed into two liters of sterile saline or water at 37° to 42° C. The pouch is left in the water bath until ice crystals are essentially dissolved. Because of the toxic effects of the dimethylsulfoxide cryopreservant at temperatures above 4° C., under no circumstances, should the pouch remain in the warming bath more than fourteen minutes. After the tissue has been thawed to 4° C., the tissue is placed into a suitable container where a series of precise dilution sequences are performed.

The following specific examples will illustrate the invention as it applies to harvesting, freezing to ultracold temperatures, and thawing of a human heart valve. It will be appreciated that other examples will be apparent to those of ordinary skill in the art and that the invention is not limited to these specific illustrative examples.

EXAMPLE 1

The heart was procured in toto using strict sterile conditions. The initial preparation and draping of the donor extended to above the jugular notch and laterally to the nipples. A midline sternotomy incision is used to expose the heart. Absence of significant aortic and mitral valve regurgitation should be confirmed by palpitation for thrills. The aorta was circumferentially dissected just distal to the origin of the innominant artery. The cavae was ligated with umbilical tapes. Next, forceful inflation of the lungs assisted in emptying the heart. The heart was everted from the pericardium and the pulmonary veins transected. After returning the heart to the pericardium, the pulmonary arteries were transected as were the cavae proximal to the ties. The aorta was ligated distal to the innominant artery and transected. The heart was placed into a basin containing 200 to 300 ml of Ringer's solution at 4° C., and as much blood as possible flushed from the heart by gently massaging the ventricles.

In preparation for transport, the heart was placed into a sterile intestinal bag with about 350 ml of Ringer's lactate at 4° C. The bag was secured with a plastic band or umbilical tape and was placed into a second intestinal bag which was likewise secured. Now the heart, which is double bagged, was placed in a nalgine or a plastic container and the lid secured. The container was then put into a third sterile intestinal bag and put into a styrofoam shipping container with wet ice.

EXAMPLE 2

The pericardial reflection was removed by creating a plane in the adventicia on the distal-most surface of the aorta, and staying anterior, dissected toward the right ventricle until the right coronary artery was identified and dissected free. The right coronary and coronal branch are carefully dissected away from the right ventricle 1 to 2 cm and transected. Using the crile forceps, the pericardial reflection is anchored to the drape and in a clockwise fashion. The adventicia is circumferentially dissected away from the entire aorta to the level of the ventricle ring. This dissection is continued to the right using the hemostats for traction until the left coronary artery was identified or approximately 100° of the circumference of the aortic route was identified.

The hemostats were removed and the distal pulmonary artery was separated from the pericardial reflection. The pulmonary artery was retracted anteriorly and anchored with a Kelly clamp to the left ventricle. The pulmonary artery was dissected counterclockwise from the origin of the right coronary between the base of the pulmonary artery and aortic annulus. The dissecting continued counter-clockwise until the left coronary artery was identified, dissected free 1 to 2 cm and transected. The pulmonary outflow tract was removed by entering the right ventricle at least 1.5 cm inferior to the base of the pulmonary artery. When the chamber of the right ventricle was entered, the scissors were directed toward the base of the right coronary artery and a full thickness cut was made through the interior wall of the right ventricle. The dissection was ended 3 mm inferior to the aortic route. Next, a shallow tract was made 1 cm distal to the origin of the pulmonary cusps and 2 mm deep across the anterior surface of the posterior wall of the right ventricle. The lower jaw point and blade of the metzenbaum dissecting scissors was used to create the tract. The pulmonary valve and artery were dissected free of the right ventricle by following the tract superior at a depth of 2 to 3 mm. When removed, the entire pulmonary outflow tract was placed in the basin of chilled Ringer's solution.

The right ventricle was dissected away from the aortic route in a clockwise direction until the membraneous septum was encountered. The chordae attached to the anterior and medial tricuspid cusps was transected, and, staying 2 to 3 mm away from the aortic route, the left atrium was entered. The left atrium was dissected away leaving 1 to 2 mm attached to the left and right fibrous trigone.

The left ventricle was entered by cutting full thickness between the mitral cusp at the commissural cusps. This exposed the left ventricle. The dissection continued to the apex. The chordae tendinae that is attached to the anterior mitral leaflet was transected and draped over the posterior aortic route. The aortic cusps were inspected for injury or defect.

Using the lower jaw of the metzenbaum dissecting scissors, a horizontal tract was made 1 cm inferior to the posterior and left aortic cusp. Traction was placed on the aortic route and the aortic homograft was dissected free of the left ventricle leaving 2 to 3 mm of thickness. Excess ventricle was carefully dissected from the aortic route and the inside diameter of the allograft was sized using Hegar dilators. The coronary arteries were tied 2 mm from the base using 20 silk. The valve's conduit was placed into a nutrient media RPMI 1640, and was ready for antibiotic sterilization.

For the pulmonary conduit, the adventitia was removed from the surface of the artery in a manner similar to that used on the aorta with the dissection beginning distally and working toward the ventricular muscle band. Finally, excess fat was trimmed off the muscle band, the pulmonary allograft was measured and then placed in the antibiotic solution with the aortic allograft.

EXAMPLE 3

The following commonly used antibiotics were added to the RPMI medium and applied to the dissected tissue:
1. Amphotericin B, 25 micrograms per ml;
2. Polymixin B Sulfate, 100 micrograms per ml;
3. Cefoxitin, 240 micrograms per ml;
4. Vancomycin, 50 micrograms per ml; and
5. Lincomycin, 120 micrograms per ml.

Investigation into the use of these antibiotics reveal that for each twenty-four hour period at 4° C. approximately 10% or more of the cells perish. Furthermore, it is known that time and temperature can severely effect the survival of cells as well.

One assay to determine whether the cells which make up the heart valve leaflet are viable is a $^3$H-proline uptake assay. A description of this procedure is as follows: The valve leaflet pieces were cut into three equal parts. The pieces were used for histology and for incubation in $^3$H-proline. Valve pieces were incubated for six hours in 5 ml of F10 medium containing 10% fetal calf serum and 15 $\mu$C of $^3$H-proline per ml (specific activity 1.0 mCi/mmol). Subsequently, the valves were incubated with cold proline and fixed in formaldehyde. Paraffin sections (5 $\mu$m) were process for dipping autoradiography using Kodak emulsion. After two weeks the film is fixed and sections stained with hematoxylin and eosin. These autoradiographs show labeling over the cells and intracellulary which represents proline or hydroxyproline containing proteins that have been secreted by the cells. Collagen is a good candidate for such an assay because the collagen contains a high concentration of proline and hydroxyproline and is the major component of valve fibroblasts. Cells not labeled with $^3$H-proline are considered to be dead. The calculation to determine viability is as follows:

(% labeled cells/labeled control) × 100% = % viable cells)

The viability of a heart valve is not only dependent on the percentage of the labeled cells but, even more, on the absolute number of labeled cells. A valve with a high number of cells and a low viability percentage can still contain a reasonable number of viable cells and a valve with a low number of cells and a high viability percentage can contain an unacceptably low number of viable cells. According to the literature, a cell is viable if 200 or more cells are labeled and counted per field of view.

Using the above-described $^3$H-proline uptake assay for cell viability, the effect of antibiotics on human heart valves was determined after a 48 hour incubation and a 24 hour incubation in the aforementioned antibiotic mixture. The results of this test are summarized in Table A.

TABLE A

|  | Time | labeled | non-labeled | Total |
|---|---|---|---|---|
| Control Valve | 48 hr | 1,505 | 241 | 1,746 |
| % total cpm |  | 81 | 19 | 100 |
| Antibiotic-treated Valve | 48 hr | 1466 | 962 | 2,428 |
| % total cpm |  | 60 | 40 | 100 |
| Survival | 60 × 100/81 = 74% |  |  |  |
| Control Valve | 24 hr | 1766 | 507 | 2,273 |
| % total cpm |  | 78 | 22 | 100 |
| Antibiotic-treated Valve | 24 hr | 1465 | 447 | 1,912 |
| % total cpm |  | 77 | 22 | 100 |
| Survival | 77 × 100/78 = 99% |  |  |  |

The data shows that there is an approximately 25% improvement in cell viability when cells are incubated in the antibiotic solution for twenty-four hour than when cells were incubated for forty-eight hours in the antibiotic solution. The control tissue was subjected to the same dissection and freezing except that no antibiotics were added during incubation in nutrient medium RPMI 1640. The study was performed using tritiated proline which is incorporated into the fibroblast cells of the valve leaflets.

EXAMPLE 4

For cryopreserving heart valves according to the present invention, it has been determined that 10% dimethylsulfoxide added to the RPMI 1640 with 10% fetal calf serum is sufficient to cryoprotect heart valves during freezing if the dimethylsulfoxide is added at temperatures of 4° C. or below. For purposes of human heart valves, the mixture of RPMI 1640 with 10% fetal calf serum and 10% dimethylsulfoxide were added without the need for titration, but it must be accomplished at 4° C. or below. One half hour of equilibration time is required before initiation of the freezing cycle.

Once the cryoprotectant was added to the freezing media, and the tissue was allowed to equilibrate at 4° C. The freezing cycle in a Controlled Rate Freezer, Model 101A (Cryomed, Mt. Clemens, MI) was started. Other standard cryogenic freezers readily known to those of ordinary skill in the art can be used. Selection of the freezing profile, i.e., the rate of cooling and variation in the rate of cooling, is very important in maintaining the viability of the heart valve cells during the freezing process.

Referring now to FIG. 1, which graphically shows the optimal freezing profile for human heart valves, the pulsating vertical bars represent the temperature of the chamber and the horizontal solid line represents the temperature of the sample of tissue. It is the horizontal factor which requires precise manipulation through the use and regulation of liquid nitrogen entering the system. Freezers using a platform Dewar system would have corresponding regulation through raising or lowering of the platform on which the freezing chamber is placed instead of opening or closing the liquid nitrogen valve. The freezing profile can be summarized as follows and is graphically depicted in FIG. 1. The sample was placed in the sample chamber at approximately 22° C. The temperature of the sample chamber was decreased at a rate of 10° C. per minute until the sample chamber has reached a temperature of −10° C. The chamber temperature was then decreased at a rate of 0.01° C. per minute until the sample temperature reaches 4° C. The chamber temperature is then cooled at 1.5° C./min until the sample if −3° C. When the sample reaches −3° C., the sample chamber was rapidly cooled to −140° C. at a rate of 95° C. per minute. When the temperature of the sample chamber reaches −140° C., the temperature was held constant for one minute. After the one-minute period, the sample chamber was warmed to −100° C. at a rate of 20° C. per minute. When the sample chamber reaches a temperature of −100° C., the temperature was held constant for six minutes. At the end of the six-minute constant temperature, the sample chamber was warmed to −32° C. at a rate of 20° C. per minute. The sample chamber was then held by −32° C. for a period of two minutes. The temperature of the sample chamber was then lowered at a rate of 1° C. per minute to a temperature of −80° C.

At the heat of fusion point, −4° C., care must be taken not to overcompensate the lowering of the tissue temperature, but to allow for a constant −1° C. per minute drop to occur. This rate of decrease and temperature for this tissue continues to a temperature of −80° C. Thereafter, the tissue was immersed into a liquid nitrogen refrigerator for long-term storage.

EXAMPLE 5

The heart valve frozen in Example 4 was thawed as follows: The foil pouch containing the allograft was placed into two liters of sterile saline or water at 37° to 42° C. The pouch was left in the water bath until ice crystals were essentially dissolved. This may be determined by gentle palpitation of the foil pouch. Because of the toxic effects of the dimethylsulfoxide at temperatures above 4° C., under no circumstances, should the pouch remain in the bath for more than fourteen minutes.

The tissue was placed into a suitable container where the following dilution sequences were performed to quickly remove the cryoprotectant:
1. RPMI plus 10% fetal calf serum plus 7.5% dimethylsulfoxide for one minute;
2. RPMI plus 10% fetal calf serum plus 5% dimethylsulfoxide for one minute;
3. RPMI plus 10% fetal calf serum plus 2.5% dimethylsulfoxide for one minute; and
4. RPMI plus 10% fetal calf serum plus 0% dimethylsulfoxide until surgery.

The above dilution sequence relies upon attention to detail in short period of time.

Once the tissue has been thawed and diluted, there was recovery phase for the tissue which is beneficial for optimum liability.

It should be understood, of course, that the foregoing relates only to a preferred embodiment of the present invention and that numerous modifications or alterations may be made therein without departing from the spirit and scope of the invention as set forth in the appended claims.

We claim:

1. A method of cryopreserving heart valves comprising the sequential steps of:
   a. dissecting a heart valve from a heart;
   b. placing the dissected heart valve into an isotonic medium with antibiotics and a cryopreservative;
   c. freezing the heart valve according to a freezing schedule that will maintain cell viability comprising the sequential steps of:
   (1) placing the dissected heart valve in a freezing chamber,
   (2) lowering the temperature of said freezing chamber at a rate of approximately 0.01° C./minute to a sample temperature of approximately +4° C.;
   (3) lowering the temperature of said freezing chamber at a rate of approximately 1.5° C./minute to a sample temperature of approximately −3° C.;
   (4) lowering the temperature of said freezing chamber at a rate of approximately 95° C./minute to a chamber temperature of approximately −140° C.;
   (5) holding the temperature of said freezing chamber at approximately −140° C. for approximately one minute;
   (6) raising the temperature of said freezing chamber to approximately −100° C. at a rate of approximately 20° C./minute;
   (7) holding the temperature of said freezing chamber at approximately −100° C. for approximately six minutes;
   (8) raising the temperature of said freezing chamber to approximately −70° C. at a rate of approximately 10° C./minute;
   (9) raising the temperature of said freezing chamber to approximately −26° C. at a rate of approximately 20° C./minute;
   (10) holding the temperature of said freezing chamber at approximately −26° C. for approximately 2 minutes; and
   (11) lowering the temperature of said freezing chamber at a rate of 1° C./minute until the temperature of the freezing chamber is approximately −80° C.; and
   d. transferring the heart valve to a storage receptacle maintained at a temperature below −132° C.

2. The method of claim 1, wherein said antibiotics comprises an effective amount of a mixture of polymixin B sulfate, cefotoxin, vancomycin, and lincomycin sufficient to substantially prevent cellular toxicity and maintain antibiotic effectiveness.

3. The method of claim 1, wherein said medium is a nutrient medium for heart valve tissue.

4. The method of claim 1 wherein said cryopreservative is dimethylsulfoxide.

5. A method of thawing a previously cryopreserved heart valve, comprising the sequential steps of:
   a. placing the frozen tissue in a sterile saline bath at a temperature of between approximately 37° C. and 42° C. for approximately 10 to 14 minutes to substantially thaw the frozen tissue;
   b. transferring the thawed tissue to a medium with approximately 7.5% by volume of cryopreservative for approximately 1 minute;
   c. transferring the thawed tissue to a medium with approximately 5% by volume of cryopreservative for approximately 1 minute; and
   d. transferring the thawed tissue to a medium with approximately 0% by volume of cryopreservative.

6. A method of cryopreserving and thawing heart valves that will maintain cell viability, comprising the sequential steps of:
   a. dissecting a heart valve from a heart;
   b. placing the dissected heart valve into a isotonic medium with antibiotics and a cryopreservative;
   c. freezing the heart valve according to a freezing schedule comprising the sequential steps of:
   (1) placing the dissected heart valve in a freezing chamber,
   (2) lowering the temperature of said freezing chamber at a rate of approximately 0.01° C./minute to a sample temperature of approximately +4° C.;
   (3) lowering the temperature of said freezing chamber at a rate of approximately 1.5° C./minute to a sample temperature of approximately −3° C.;
   (4) lowering the temperature of said freezing chamber at a rate of approximately 95° C./minute to a chamber temperature of approximately −140° C.;
   (5) holding the temperature of said freezing chamber at approximately −140° C. for approximately one minute;
   (6) raising the temperature of said freezing chamber to approximately −100° C. at a rate of approximately 20° C./minute;
   (7) holding the temperature of said freezing chamber to approximately −100° C. for approximately six minutes;
   (8) raising the temperature of said freezing chamber to approximately −70° C. at a rate of approximately 10° C./minute;
   (9) raising the temperature of said freezing chamber to approximately −26° C. at a rate of approximately 20° C./minute;
   (10) holding the temperature of said freezing chamber to approximately −26° C. for approximately 2 minutes; and
   (11) lowering the temperature of said freezing chamber at a rate of 1° C./minute until the temperature of the freezing chamber is approximately −80° C.;
   (d) transferring the heart valve to a storage receptacle maintained at a temperature below −132° C.; and
   (e) thawing the frozen tissue by the sequential steps of:
   (1) placing the frozen tissue in a sterile saline bath at a temperature of between approximately 37° C. and 42° C. for approximately 10 to 14 minutes to substantially thaw the frozen tissue;
   (2) transferring the thawed tissue to a medium with approximately 7.5% by volume of cryopreservative for approximately 1 minute;
   (3) transferring the thawed tissue to a medium with approximately 5% by volume of cryopreservative for approximately 1 minute; and
   (4) transferring the thawed tissue to a medium with approximately 0% by volume of cryopreservative.

7. The method of claim 6, wherein said antibiotics comprises an antibiotically effective amount of a mixture of polymixing B sulfate, cefotoxin, vancomycin, and lincomycin sufficient to substantially prevent cellular toxicity and maintain antibiotic effectiveness.

8. The method of claim 6, wherein said medium is a nutrient medium for heart valve tissue.

9. The method of claim 6, wherein said cryopreservative is dimethylsulfoxide.

10. The method of claim 6, further comprising the additional step, immediately following step e(3), of transferring the frozen tissue to a medium with approximately 2.5% by volume of cryopreservative for approximately 1 minute.

* * * * *